(12) United States Patent
Hansen et al.

(10) Patent No.: US 10,434,288 B2
(45) Date of Patent: Oct. 8, 2019

(54) LOCKING MEDICAL GUIDE WIRE

(71) Applicant: Cook Medical Technologies LLC, Bloomington, IN (US)

(72) Inventors: Palle Munk Hansen, Bjaeverskov (DK); Per Hendriksen, Herlufmagle (DK); Raimo Urban Butzbacker, Hasley (DK)

(73) Assignee: Cook Medical Technologies LLC, Bloomington, IN (US)

( * ) Notice: Subject to any disclaimer, the term of this patent is extended or adjusted under 35 U.S.C. 154(b) by 87 days.

(21) Appl. No.: 15/411,504

(22) Filed: Jan. 20, 2017

(65) Prior Publication Data

US 2017/0224964 A1   Aug. 10, 2017

Related U.S. Application Data

(63) Continuation-in-part of application No. 15/405,883, filed on Jan. 13, 2017, now abandoned.

(30) Foreign Application Priority Data

Jan. 15, 2016 (GB) .................................. 1600797.3

(51) Int. Cl.
  *A61B 5/00* (2006.01)
  *A61M 25/09* (2006.01)

(52) U.S. Cl.
  CPC ..... *A61M 25/09* (2013.01); *A61M 2025/0915* (2013.01); *A61M 2025/09125* (2013.01); *A61M 2205/0216* (2013.01)

(58) Field of Classification Search
  CPC ..... A61M 25/04; A61M 25/09; A61M 1/1034
  (Continued)

(56) References Cited

U.S. PATENT DOCUMENTS

| | | |
|---|---|---|
| 2,494,260 A | 1/1950 | Osmond |
| 3,625,200 A | 12/1971 | Muller |

(Continued)

FOREIGN PATENT DOCUMENTS

| | | |
|---|---|---|
| DE | 199 10 128 D1 | 1/2001 |
| WO | WO 97/21475 A1 | 6/1997 |

OTHER PUBLICATIONS

Combined Search and Examination Report, dated Jun. 23, 2016, pp. 1-7, issued in Great Britain Application No. GB160079.3, Intellectual Property Office, South Wales.

(Continued)

*Primary Examiner* — May A Abouelela
(74) *Attorney, Agent, or Firm* — Brinks Gilson & Lione (57) ABSTRACT

A guide wire includes a plurality of segments which can interlock rotatably relative to one another. A locking element extends through a lumen of the segments. When the locking element is in an unlocked condition the segments are able to rotate relative to one another. In this mode, the guide wire is very flexible. The locking element can be tightened to cause the segments to lock in engagement with one another and to fix the guide wire in position. In practice, the guide wire can be fixed in a curved or bent configuration, which enables the guide wire to provide a rigid support for a microcatheter or other element of an introducer assembly. The guide wire therefore can exhibit both extreme flexibility and stiffness.

17 Claims, 8 Drawing Sheets

(58) Field of Classification Search
USPC .................................. 600/300, 585, 146, 411
See application file for complete search history.

(56) References Cited

U.S. PATENT DOCUMENTS

| | | | |
|---|---|---|---|
| 3,858,578 A | 1/1975 | Milo | |
| 4,294,260 A | 10/1981 | Veatch | |
| 4,949,927 A * | 8/1990 | Madocks | F16M 11/40 248/160 |
| 4,955,384 A | 9/1990 | Taylor et al. | |
| 5,902,254 A | 5/1999 | Magram | |
| 6,682,493 B2 | 1/2004 | Mirigian | |
| 7,041,052 B2 * | 5/2006 | Saadat | A61B 1/0008 600/114 |
| 7,250,027 B2 * | 7/2007 | Barry | A61B 1/0056 600/139 |
| 7,634,874 B2 * | 12/2009 | Lucas | E04H 4/082 52/108 |
| 7,682,319 B2 * | 3/2010 | Martin | A61B 17/00234 600/139 |
| 7,758,520 B2 * | 7/2010 | Griffin | A61M 25/00 600/434 |
| 8,246,575 B2 * | 8/2012 | Viola | A61B 1/00147 604/95.04 |
| 8,298,161 B2 * | 10/2012 | Vargas | A61M 25/00 600/587 |
| 8,348,834 B2 * | 1/2013 | Bakos | A61B 17/3417 600/114 |
| 8,758,270 B2 * | 6/2014 | Ryan | F16D 3/52 600/585 |
| 8,845,524 B2 * | 9/2014 | Belson | A61B 1/0053 600/103 |
| 8,992,421 B2 * | 3/2015 | Stand | A61B 1/0057 600/139 |
| 9,113,783 B2 * | 8/2015 | Suehara | A61M 39/1055 |
| 9,463,022 B2 * | 10/2016 | Swayze | A61B 17/1155 |
| 9,585,651 B2 * | 3/2017 | Lam | A61B 17/0401 |
| 9,668,641 B2 * | 6/2017 | Ostrovsky | A61B 1/0055 |
| 9,808,140 B2 * | 11/2017 | Belson | A61B 1/00004 |
| 9,980,778 B2 * | 5/2018 | Ohline | A61B 90/98 |
| 2002/0120178 A1 | 8/2002 | Tartaglia et al. | |
| 2003/0105415 A1 | 6/2003 | Mirigian | |
| 2003/0233058 A1 * | 12/2003 | Ewers | A61B 1/0008 600/585 |
| 2004/0186350 A1 | 9/2004 | Brenneman et al. | |
| 2004/0254450 A1 * | 12/2004 | Griffin | A61M 25/00 600/411 |
| 2006/0089532 A1 | 4/2006 | Tartaglia et al. | |
| 2006/0178562 A1 * | 8/2006 | Saadat | A61B 1/0055 600/142 |
| 2006/0200000 A1 * | 9/2006 | Sato | A61B 1/0055 600/146 |
| 2007/0135683 A1 * | 6/2007 | Bob | A61B 1/00082 600/144 |
| 2009/0099554 A1 | 4/2009 | Forster et al. | |
| 2010/0305475 A1 * | 12/2010 | Hinchliffe | A61M 25/09 600/585 |
| 2011/0207999 A1 | 8/2011 | Torisawa et al. | |
| 2012/0143175 A1 | 6/2012 | Hermann et al. | |
| 2012/0191012 A1 | 7/2012 | Chin et al. | |
| 2014/0166718 A1 * | 6/2014 | Swayze | A61B 17/1155 227/175.1 |
| 2015/0216589 A1 | 8/2015 | Wittenberger et al. | |
| 2016/0135663 A1 * | 5/2016 | Isoda | A61B 1/0057 600/103 |

OTHER PUBLICATIONS

Extended Search Report in corresponding European Application No. 17275003.6, dated May 31, 2017, 10 pages.
Extended European Search Report, dated May 23, 2018, pp. 1-9, issued in European Patent Application No. 18275005.9, European Patent Office, Berlin, Germany.
United Kingdom Search and Examination Report, dated May 9, 2018, pp. 1-8, issued in United Kingdom Patent Application No. GB1720416.5, Newport, South Wales, United Kingdom.
GB Examination Report, dated Jan. 31, 2019, pp. 1-4, issued in Great Britain Application No. GB1600797.3, Intellectual Property Office, South Wales.
GB Examination Report dated Apr. 2, 2019, pp. 1-7, issued in Great Britain Application No. GB1720416.5, Intellectual Property Office, South Wales.

* cited by examiner

LOCKING MEDICAL GUIDE WIRE

CROSS-REFERENCE

The present application claims priority to U.S. patent application Ser. No. 15/405,883, "Locking Medical Guide Wire" filed on Jan. 13, 2017, which in turn claims priority to United Kingdom Patent Application No. 1600797.3, "Locking Medical Guide Wire", filed Jan. 15, 2016, of which both are incorporated by reference in their entirety.

TECHNICAL FIELD

The present disclosure relates to a locking medical guide wire assembly for use, for example, in endoluminal medical procedures.

BACKGROUND

Endoluminal medical procedures are now common in many countries as they can significantly reduce clinical procedure times, can effect localised treatments, and can significantly reduce patient trauma and convalescence. Many techniques, including the well-established Seldinger procedure, make use of a guide wire which is fed from a remote percutaneous entry point through the patient's vasculature to the site to be treated. The treatment could be in a major vessel, such as the aorta or vena cava, but increasingly may be within a very small and delicate vessels such as the cerebral vessels.

Generally, the guide wire is the first element of an introducer assembly which is positioned at the treatment site, with the other elements of the introducer assembly subsequently being fed over the guide wire from the same percutaneous entry point. For this purpose, it is important that the guide wire is sufficiently soft, particularly at its distal end, in order to be able to curve through the patient's vasculature and into and through any branch vessels. However, it is also important for the guide wire to exhibit some strength, or rigidity, so that it can effectively guide the subsequently deployed elements of the introducer assembly through the tortuous paths of the patient's vasculature. Often, this leads to the guide wire having to exhibit contradictory characteristics of softness and strength. In some circumstances, such as in neurological applications, it is not possible or optimal to compromise on softness and strength, with the result that it becomes necessary to use in the same procedure a plurality of guide wires having different characteristics.

SUMMARY

The present disclosure seeks to provide an improved guide wire. The term guide wire or guide wire device is used herein in its general form. A variety of types of guide wire are known, such as: of simple wire core form; as an assembly of a wire core and outer layer that may be a polymer coating or coiled wire tubing; as a series of inter-linked elements able to pivot relative to one another on a wire carrier; and so on. The term guide wire is therefore to be understood to refer to the guide element of an introducer assembly which is used to guide the subsequent passage of introducer assembly components such as catheters, medical device carriers, diagnostic tools, protective sheaths and so on.

According to an aspect of the present disclosure, there is provided a medical guide wire of elongate form and having a longitudinal dimension, a distal end and a proximal end; at least the distal end of the guide wire being formed of a plurality of inter-cooperating elements disposed longitudinally in series, the inter-cooperating elements having cooperating curved facing surfaces which are able to slide relative to one another so as to cause the distal end of the guide wire to be bendable in at least one lateral dimension; the cooperating curved surfaces forming a unitary device in which the inter-cooperating elements do not disassemble from one another; the cooperating facing surfaces being lockable in non-sliding manner to one another; and a locking mechanism coupled at the distal end of the guide wire and operable to lock the cooperating facing surfaces together so as to lock the distal end of the guide wire in a straight or bent configuration.

The assembly provides a guide wire which can be very soft, that is able to flex sideways with very little resistance, yet able to be locked in position in order to make it stiff. In its soft configuration, the guide wire is able to pass through tortuous vasculature without damaging or causing trauma to the vessel walls. The preferred embodiments are particularly suited to neurological applications, that is delicate cerebral vessels. In its locked configuration, the guide wire can be set into a generally rigid shape and thus able to provide a good support for stiffer elements of an introducer assembly. These may be any of the elements discussed above.

Advantageously, the cooperating facing surfaces are rounded, preferably part-circular. This shape optimises the bendability of the guide wire.

The cooperating facing surfaces of the elements may be, respectively, convex and concave. They preferably lie in planes substantially perpendicular to the longitudinal axis of the device.

The cooperating facing surfaces may be textured, toothed or friction surfaces. That is, the surfaces do not slide relative to one another when pushed together.

In an embodiment, the guide wire includes at least three inter-cooperating elements having a plurality of sets of cooperating surfaces, each set of cooperating surfaces being located at adjacent inter-cooperating elements.

Some or all of the sets of cooperating surfaces may be disposed along a common line parallel to the longitudinal dimension or along different lines parallel to the longitudinal dimension.

In the preferred embodiment, the locking element applies a longitudinally extending constraining force on the inter-cooperating elements.

The inter-cooperating elements may each have a channel therein, the channels being arranged in series with one another to form an elongate lumen. In this embodiment, the locking element extends through in the channels of the inter-cooperating elements. For this purpose, the locking element may be a wire or cable connected at the distal end of the guide wire. The locking element may be made of a metal or metal alloy, of carbon fibre, of a strong polymer material or of fibrous material, either synthetic and natural. For larger diameter devices the locking element may be made of a stretchable or elastomeric material such as silicone.

The locking mechanism is advantageously connected to a driving element at the proximal end of the guide wire. An example is a pull handle or the like. In other embodiments, the locking mechanism may be mechanically driven, such as by an electric motor, a spring and so on.

In some embodiments each inter-cooperating element includes a wall or shoulder substantially transverse to the longitudinal direction to prevent decoupling of the element to an adjacent element.

In some embodiments, the inter-cooperating elements snap-fit to one another.

There may be provided a covering sleeve or sheath disposed over the inter-cooperating elements. In practice, a sleeve can ensure a smooth outer surface to the guide wire.

Other aspects and advantages of the teachings herein will become apparent from the description of the preferred embodiments which follows.

BRIEF DESCRIPTION OF THE DRAWINGS

Embodiments of the present disclosure are described below, by way of example only, with reference to the accompanying drawings, in which.

DETAILED DESCRIPTION

Various embodiments of medical guide wire assembly are described below and shown in the accompanying drawings. It is be understood that the drawings are schematic only and are not intended to show the various components of the assembly to scale. In many cases, the assembly has been depicted in enlarged form for the sake of clarity of disclosure. The skilled person will appreciate that the assembly may be configured to a variety of different sizes, and shapes, in order to correspond to the vessel or other organ in which the device is to be deployed. In practical embodiments, the guide wire assembly can be produced to have a very small diameter, including of less than a millimeter, particularly when manufactured by laser cutting a tube.

Figure 1:
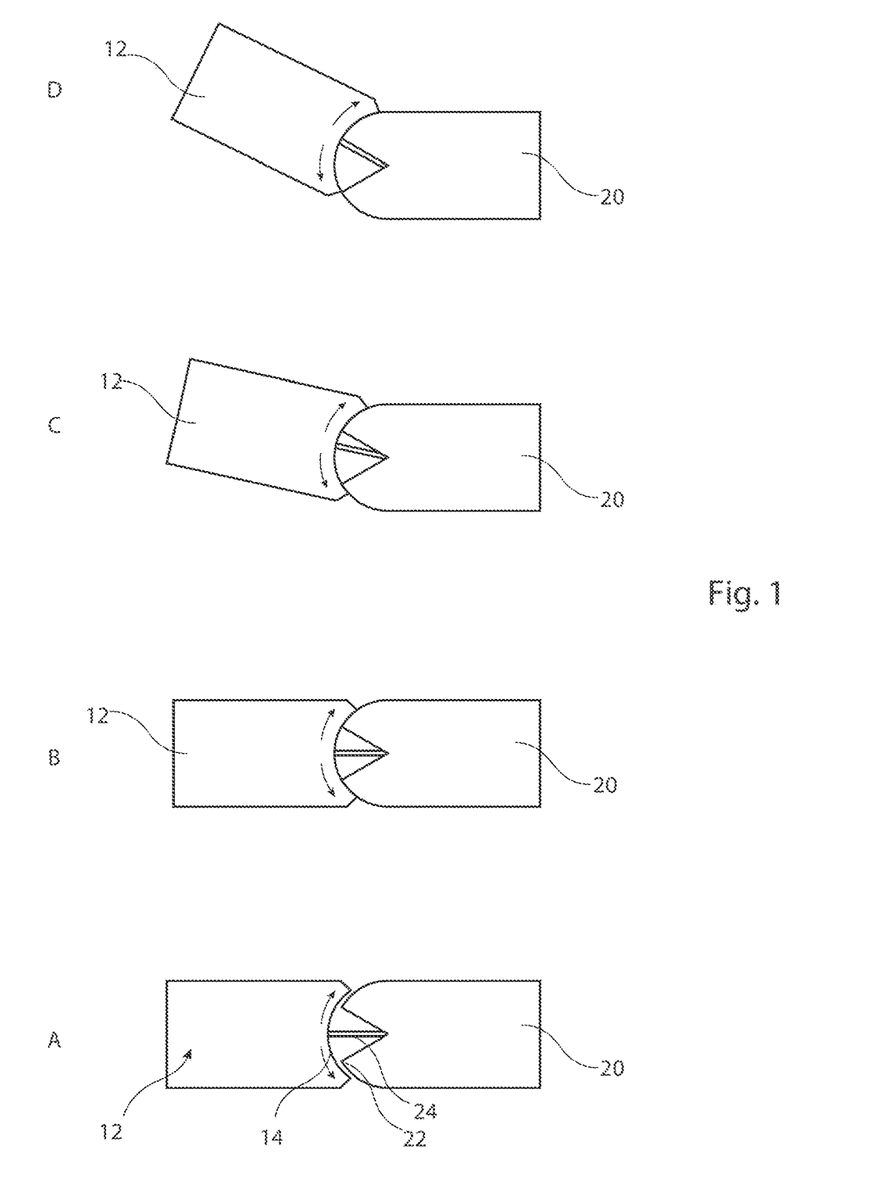
FIG. 1 is a schematic diagram showing the principle of operation of embodiments of the guide wire assembly disclosed herein.

Referring first to FIG. 1, this is a schematic diagram depicting the principles of operation, in general terms, of embodiments of guide wire taught herein.

The guide wire, which is in practice an assembly of components, includes a plurality of pivotable or rotatable elements of which two are shown in FIG. 1. A first element 12 has a concave contact surface 14, preferably being part-spherical. The second element 20 has a convex surface 22 which is also part-spherical and has a radius of curvature which matches or substantially matches the radius of curvature of the concave surface 14. The two contact surfaces 14, 22 face one another and may lie in planes which are perpendicular to the longitudinal axis of the device (when straight).

The surfaces 14, 22 are able to engage with one another in non-sliding manner so as to lock the elements 12 and 20 together non-rotatably. For this purpose, the surfaces 14 and 22 may be roughened, may have corresponding keying elements such as inter-engaging teeth or other relief patterns, may simply make friction contact with one another, and so on.

Each element 12, 20 has an internal channel or lumen therein, not visible in FIG. 1, within which there is disposed a locking element which in this example is a wire or thread 24. The locking element 24 is fixed at or proximate at least one end of the assembly of elements 12, 20 and is able to be loosened and tightened to effect a selective locking action on the elements 12, 20. For this purpose, the most distal element 12, 20, at the distal tip of the guide wire, need not have a lumen passing therethrough and in the preferred embodiments simply fixes the distal end of the locking element, for instance in a blind bore; although in other embodiments there may be provided a dedicated distal element for this purpose.

The left-most sketch of FIG. 1, that is view A, shows the elements 12, 20 in a condition in which they are loosely arranged relative to one another, that is with the locking element 24 in what could be described as an unlocked configuration. In this state, the surfaces 14, 22 may be spaced from one another or otherwise in contact but with no or no appreciable contact force between them. The elements 12, 20 could be said to be in an open or relaxed configuration. In this configuration, the surfaces 14, 22 are not pressed together and are able to slide over one another, such that the elements 12, 20 can rotate or pivot relative to one another. When the contact surfaces 14, 22 are part-spherical, the elements 12, 20 are able to pivot or rotate in any direction relative to one another, in the manner of a universal joint.

The surfaces 14, 22 may, in some embodiments, have different shapes in order to limit their angular rotation relative to one another. For instance, the surfaces 14, 22 could be at least part-cylindrical so as to rotate around a single axis of rotation, or could be shaped to rotate along two or more axes of rotation, or the like. It is preferred, though, that the surfaces 14, 22 are part-spherical.

In sketch B of FIG. 2, the locking element 24 has been engaged, that is tightened, in order to press the surfaces 14, 22 together and in particular into locking engagement. In this condition the elements 12, 20 could said to be closed. In the configuration shown, the surfaces 14, 22 are not able to slide relative to one another and are therefore locked in position. The third and fourth sketches of FIG. 1, that is sketches C and D, show the elements 12, 20 locked together at different angles. In practice, as will become apparent, the assembly can be rotated to any desired configuration within the permitted range of movement and then locked in that configuration by tightening the locking element 24, with the elements 12, 22 becoming fixed in that configuration. The assembly is such that the locking element 24 can be released, or unlocked, again so to allow the elements 12, 20 to rotate once more relative to one another. In this manner, and as will become apparent below, the assembly can be selectively loosened to be flexible and locked to as to be fixed rigid in a chosen configuration. The skilled person will appreciate that the guide wire assembly taught herein need not be fixed in a totally immovable manner and that in some embodiments at least the elements may be movable even when the locking element 24 is engaged, but only on the application of a significant force, preferably notably larger that the forces imparted to it by the other elements of an associated introducer assembly which are fed over the guide wire.

Figure 2A:
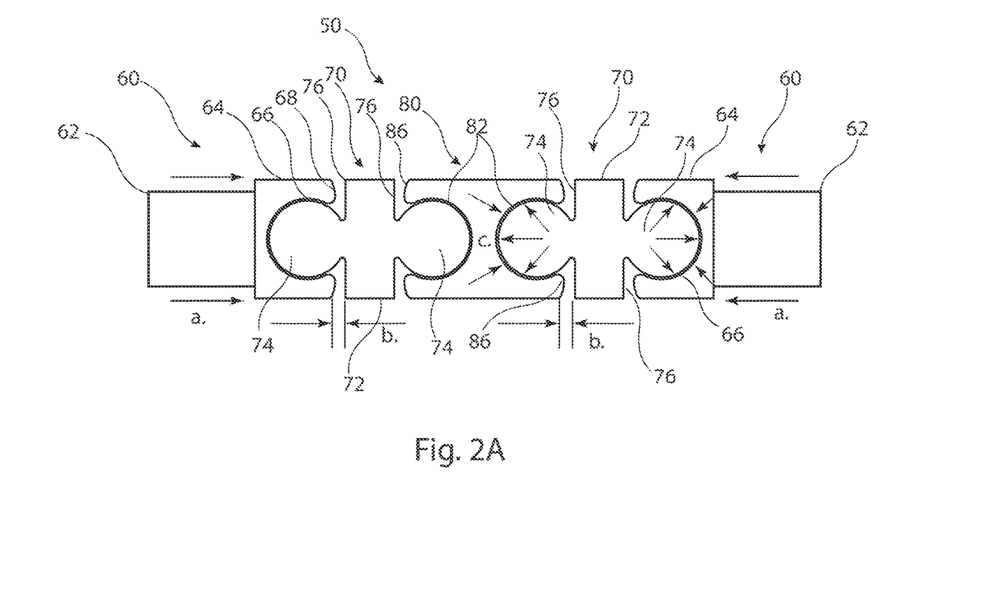
FIGS. 2A and 2B show in schematic form an embodiment of guide wire assembly according to the teachings herein.
Figure 2B:
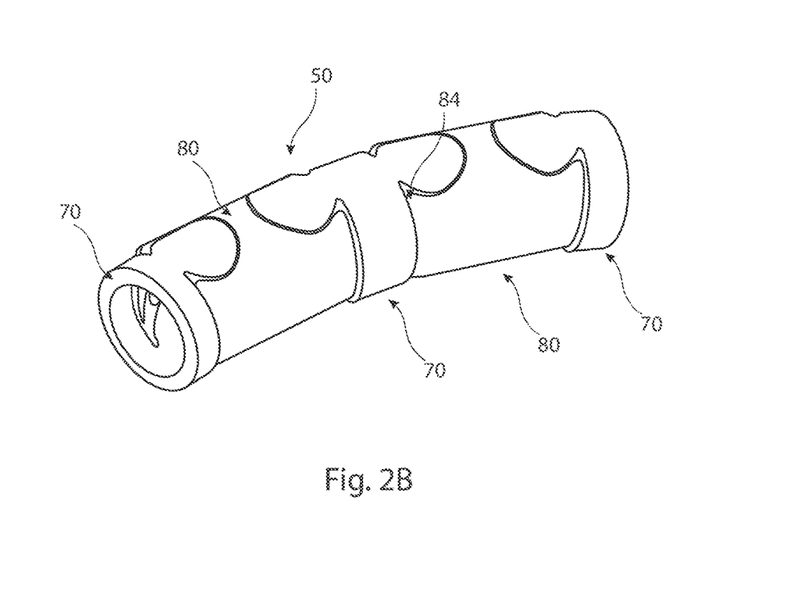

Referring now to FIGS. 2A and 2B, these show two views of a first embodiment of guide wire assembly according to the teachings herein and making use of the principles disclosed above in connection with FIG. 1. The assembly 50 includes a plurality of elements 60, 70 and 80 coupled together, as described in further detail below, to form a structure that can be very flexible but that can also be fixed in position. FIGS. 2A and 2B show only shortened versions of the assembly and it is to be understood that in practice the guide wire may be made of a greater number of the elements 60-80 and in particular of the intermediate elements 70 and 80, specifically to create a desired length of guide wire towards the distal end thereof which has the characteristics of flexibility and stiffness which are achievable by the teachings herein.

The assembly 50 has what could be described as a tubular form, as will be apparent from the perspective view of FIG. 2B, such that it has a channel or lumen 90 passing through the assembly 50, for receiving a locking element of the type shown in connection with FIG. 1. For this purpose, each element 60-80 of the assembly 50 has a passage therethrough, which when combined with the other elements forms the channel 90. It is preferred that the elements and as a result the assembly 50 are generally circular in axial cross-section.

The elements 60 could be described as end pieces and each is formed, in this example, of a coupling boss 62 and a connector portion 64. The boss 62, which is also circular in axial cross-section, has an outer diameter which is slightly smaller than the outer diameter of the connector portion 64.

Figure 5:
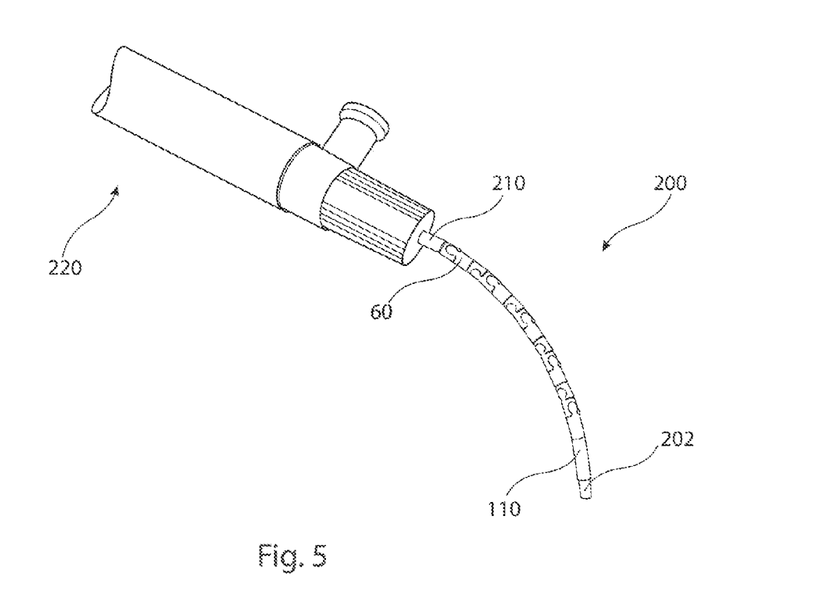
FIGS. 5 to 8 show a prototype guide wire device having a structure as shown in FIG. 4.
Figure 6:
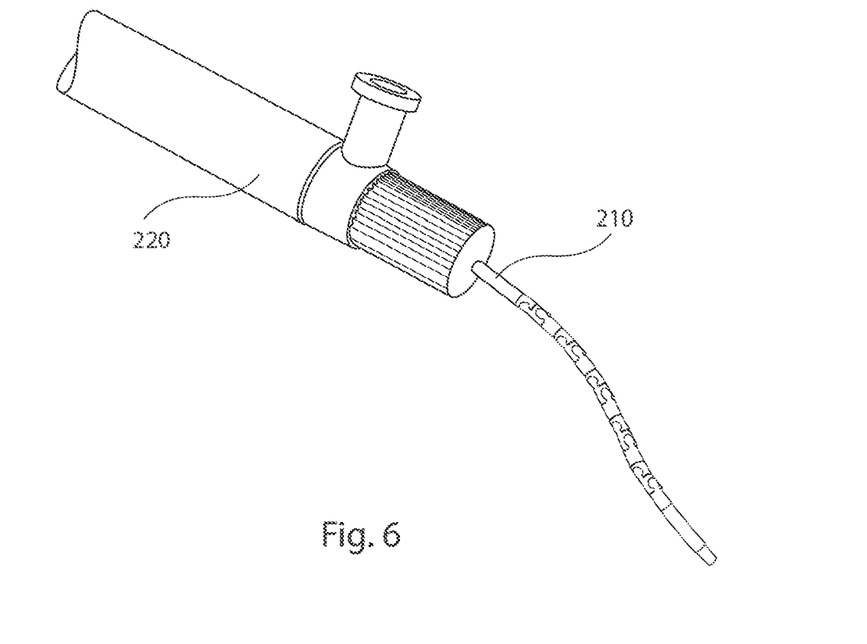
Figure 7:
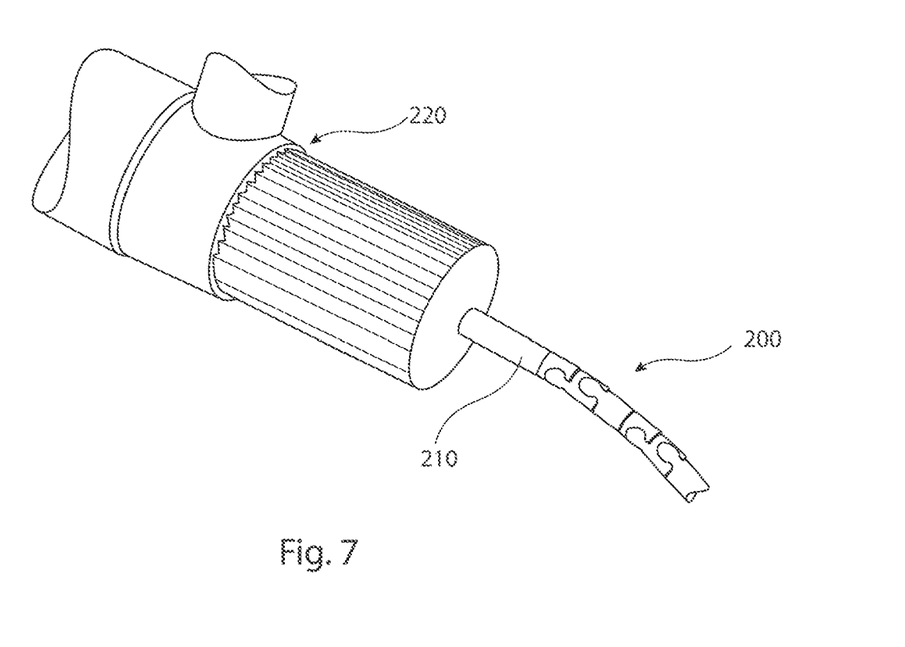
Figure 8:
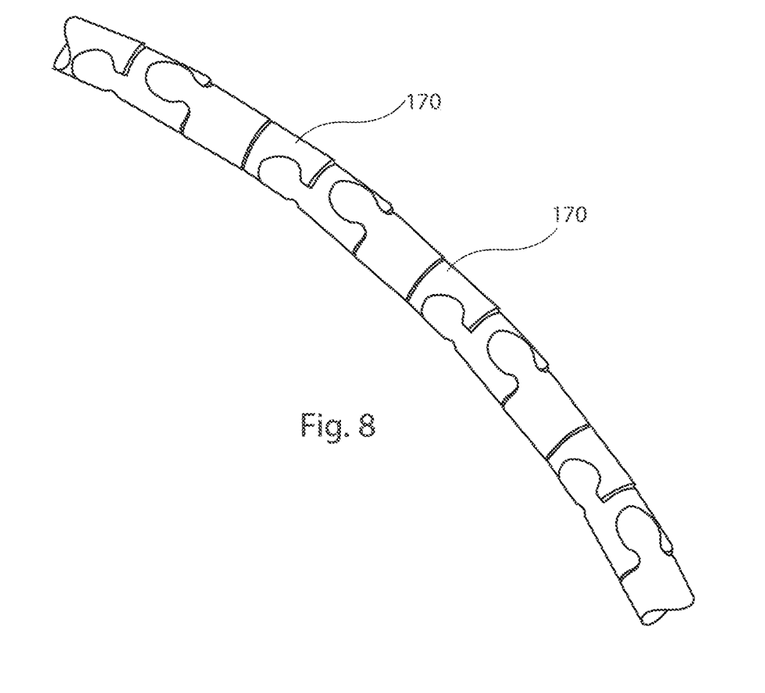

The boss 62 may be sized to fit into a proximal catheter element (not shown in FIG. 2) of the guide wire and preferably such that the outer surface of the catheter has a diameter substantially the same as the diameter of the connector portion 64, such that there is no edge or shoulder between the two when the guide wire is in its fully assembled form. The other end piece 60 can be coupled to a soft tip, an example of which is shown in FIGS. 5 and 6. Again, the soft tip could have a bore or recess for receiving the boss 62 and an outer diameter which substantially matches the outer diameter of the connector portion 64 so as to provide a smooth outer surface to the assembly.

The connector portion 64 includes a generally circular concave cut-out 66 and in practice will include two such cut-outs, diametrically opposite one another within the circular cylindrical wall of the connector portion 64. It will be appreciated that the circular cut-outs 66 also curve with the cylindrical surface of the connector portion 64. The surfaces 66 are greater than a semi-circle, thereby in practice to trap a circular head 74 of the element 70 with which it cooperates, as will be apparent from both FIGS. 2A and 2B.

The circular cut-outs 66 within the wall of the connector portion 64 have a contact surface with the characteristics mentioned above in connection with FIG. 1. More specifically, the internal surfaces of the circular cut-outs 66 may be roughened, textured or otherwise be subject to friction when the surfaces are pressed together.

The connector element 70 includes an annular central section 72, from which extend two pairs of circular enlarged heads 74, on either side of the central section 72. It will be appreciated that the circular heads 74 also curve around the circumferential periphery of the elements 60-80, as will be apparent from the perspective view of FIG. 2A. The circular heads 74 preferably have a circular end surface having a radius of curvature which is only slightly smaller than the radius curvature of the circular recesses 66. The difference in radii need only be sufficient to enable the enlarged heads 74 to rotate within their respective circular recesses 66 when in the unlocked condition. The contact surfaces of the enlarged heads 74 preferably have the surface characteristics of roughness, texturing or friction mentioned herein.

In the embodiment shown, the annular central section 72 of the element 70 has proximal and distal surfaces 76 which are substantially flat and in practice perpendicular to the longitudinal dimension of the assembly 50. The connector portion 64, on the other hand, has frontal surfaces 68 which are spaced from and taper slightly away from the end surfaces 76 of the annular central section 72. This gap, identified as b in the side elevational view of FIG. 2A, provides the space allowing rotation of the elements 60 and 70 relative to one another.

The assembly 50 also includes a female coupling element 80 which includes proximal and distal circular recesses 82, which preferably have the same characteristics as the recesses 66 of the end pieces 60, that is being the same size and having the same surface characteristics. The coupling element 80 has proximal and distal end faces 86 which are spaced from and taper from the end faces of the annular central section 72 of the connector element 70, such as to have a gap b similar to that between the end pieces 60 and element 70.

The elements 60, 70 and 80 couple to one another not only so as to form a unitary device which will not disassemble unintentionally but also in which the various elements 60-80 are able to rotate relative to one another. The facing surfaces of the recesses 66, 82 and of the enlarged heads 74 have the characteristics described above in connection with the example of FIG. 1, namely that when they are not pressed together they are able to slide over one another, yet when pressed together by the locking mechanism become fixed relative to one another, that is unable to slide, and as the result will remain in that fixed position until unlocked.

The elements or segments 60-80 may be made of a metal or metal alloy, which provides strength to the guide wire and the ability to lock the elements securely to one another. Other embodiments may use different materials for the elements for the guide wire, including polymer materials such as plastics materials. All embodiments disclosed herein may have elements with these characteristics.

The perspective view of FIG. 2B shows a portion of a guide wire assembly having the characteristics depicted in the side elevational view of FIG. 2A, but which includes, in the section visible in the perspective view, two double female elements 80 and three enlarged head elements 70, of which only a half of each of the elements 70 at the end of the section shown in FIG. 2B is visible. In practice, the two enlarged head sections 70, which can be seen at the extremities of the portion shown in the perspective view of FIG. 2B will be double ended and coupled to further elements 80 or 60 as appropriate.

The circular heads 74 and recesses 66, 82 are, as will be apparent in the two views of FIG. 2, aligned along common longitudinal lines on opposing sides of the assembly 50. In practice this allows the elements 60-80 to rotate in only two opposing directions, which could be described as providing a single degree of flexibility.

In practice, the angles by which each element or segment 60-80 can rotate relative to its adjacent elements can be chosen to be a maximum of 1-30°, depending upon the overall flexibility desired for the guide wire. The maximum angle of rotation or pivot of one element relative to another will be dependent upon the amount by which the surfaces 68, 86 of the section 60-80 are cut back or scalloped. A greater distance b will allow greater rotation of adjacent elements, whereas a smaller gap b will allow for smaller rotation.

It is to be understood that the gap b allowing rotation of adjacent segments can also be produced by cutting back or scalloping the faces 76 of the double headed elements 70 or by creating a neck between the annular central section 72 and the enlarged heads 74, for example.

Figure 3A:
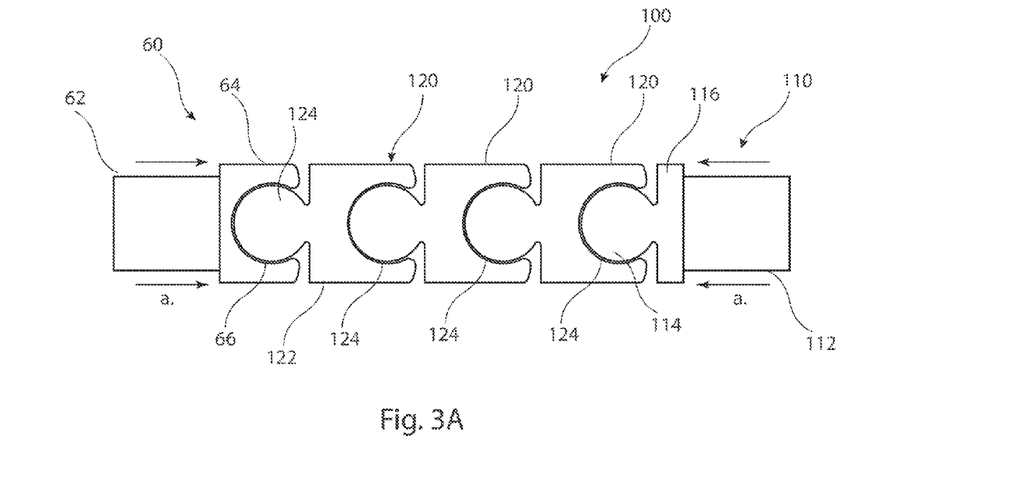
FIGS. 3A and 3B show in schematic form another embodiment of guide wire assembly according to the teachings herein.
Figure 3B:
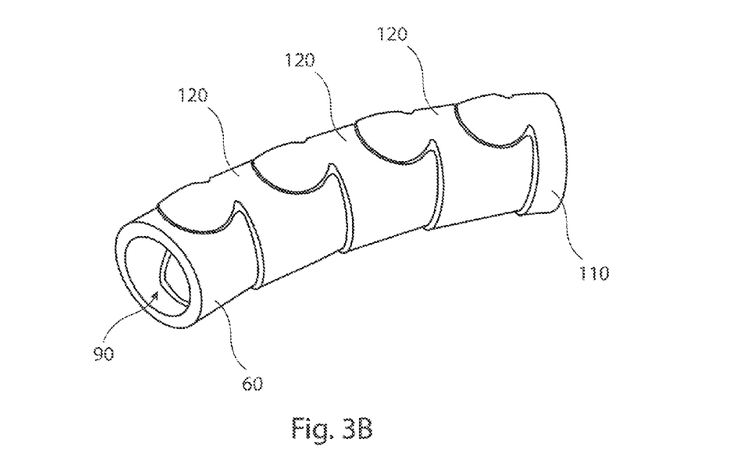

Referring now to FIGS. 3A and 3B, these show another embodiment of assembly 100 for forming a guide wire as taught herein. The assembly 100 has characteristics very similar to those of the embodiments of FIGS. 2A and 2B, although makes use of rotating elements of a different shape. The assembly 100 has a first end piece 60 which is similar to the end piece 60 of the embodiment of FIG. 2A. At the other extremity of the assembly 100 there is provided an end elements 110 having a boss 112 similar to the boss 62, but instead of a recessed connecting portion 64 has a connecting portion 114 formed of a pair of enlarged circular heads extending from the annular base 116.

The assembly 100 also includes a plurality of intermediate elements 120 which in this embodiment are all the same. Each element or segment 120 includes a cylindrical section 122 having two circular recesses 124 (on opposing sides) which are similar to the circular recesses 66 and 82 of the embodiment of FIG. 2. At the other end of each element 120 there are two circular enlarged heads 124, having characteristics similar to the enlarged heads 74 of the embodiment of FIG. 2. The enlarged heads 114, 124 and recesses 66, 124 have facing surfaces which are able to slide relative to one another when the assembly 100 is unlocked but which lock to one another in non-rotating manner when the assembly 100 is locked in place. As will be appreciated, any number of intermediate elements 120 can be provided to alter the length of the sectioned portion of the guide wire.

The perspective view of FIG. 3B shows the end pieces 60 and 110 without their respective cylindrical bosses 62, 112. Again, as with the embodiment of FIG. 2, the assembly 100 of FIG. 3 is preferably circular in axial cross-section, although could be of non-round shape, such as oval.

The assembly 100 includes a lumen 90 extending therethrough, for which the bosses 62, 112 will have channels therein, as do the bosses 62 of the embodiment of FIG. 2. Similarly, as with the embodiment of FIG. 2, the assembly 100 shown in FIG. 3 rotates in a single dimension as a result of the enlarged heads and circular recesses being aligned longitudinally with respect to one another.

As with the embodiment of FIG. 2, it is preferred the angle of rotation of adjacent sections is preferably limited to a maximum of between 1-30°, in dependence upon the preferred final bending characteristics desired for the guide wire.

Figure 4:
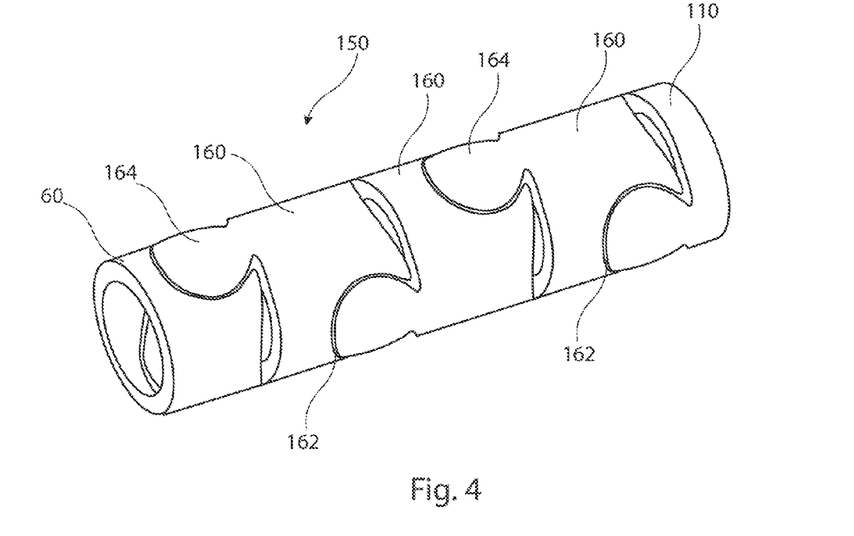
FIG. 4 shows in schematic form another embodiment of guide wire assembly according to the teachings herein.

Referring now to FIG. 4, this shows another embodiment of assembly 150 for forming a guide wire as taught herein. Its basic structure is very similar to the assemblies shown in FIGS. 2 and 3 and in particular the assembly of FIG. 3. The primary difference is that the assembly of FIG. 4 is constructed so as to be able to rotate in a plurality of dimensions. FIG. 4 shows a perspective view of an example assembly similar to the perspective view shown in FIG. 3 and in which the end pieces 60 and 110 have the same characteristics as the end pieces 60 and 110 of the embodiment of FIG. 3. The skilled person will appreciate that the bosses 62 and 112 have not been shown in FIG. 4.

The intermediate elements 160 are similar in construction to the elements 120 of the embodiment of FIG. 3 save for the fact that in each element the pairs of enlarged heads 164 are offset relative to the circular recesses 162 by 90°. The elements 160 therefore couple to one another at a 90° offset. The structure is such that the enlarged heads 164 of every other element 160 are aligned, as are the circular recesses 162. As a result, at one end of each element 160 there is rotation in one dimension (for instance rotation around an axis formed by the opposing enlarged heads 164) while at the other end the rotation is at 90° to this (around the axis of the circular recesses 162 of that same element 160). As a consequence, the structure of FIG. 4 is able to flex in many more directions than the examples of FIGS. 2 and 3.

It will be appreciated that a guide wire will be formed of any number of elements 160 required to provide the desired length of flexible and lockable section at the distal end of the guide wire.

It will be appreciated that it is not necessary for the recesses and enlarged heads of each element 160 to be offset by 90° from one another, as they could be offset by a different amount, for example 60° or the like, in which case the assembly 150 will rotate in different dimensions.

Referring now to FIGS. 5 to 8, these show a prototype guide wire assembly incorporating the guide wire 200. The assembly includes, in the prototype examples shown in FIGS. 5 to 8, a short catheter portion 210 at the proximal end of the guide wire, although it is to be understood that in practice this will be longer and may also be flexible. In some embodiments, the catheter section 210 may comprise the major portion of the length of the guide wire, with only the distal end of the guide wire being made of the rotatable elements. In other embodiments, the majority of the guide wire may be made of rotatable elements with the catheter portion 210 being relatively short and provided primarily to assist in the locking action and with the coupling to the control handle 220.

The guide wire 200 is formed of a plurality of rotatable elements 170 having characteristics very similar to the elements 160 of the embodiment of FIG. 4, that is in which the elements have enlarged circular heads which are offset by 90° to the circular cut-outs in the elements, so as to enable the assembly to rotate in a plurality of dimensions.

At the distal end of the guide wire 200 there is provided a soft tip 202, attached to the end piece 110 and which in practice may hold the distal end of a locking element, described in further detail below.

Figure 9:
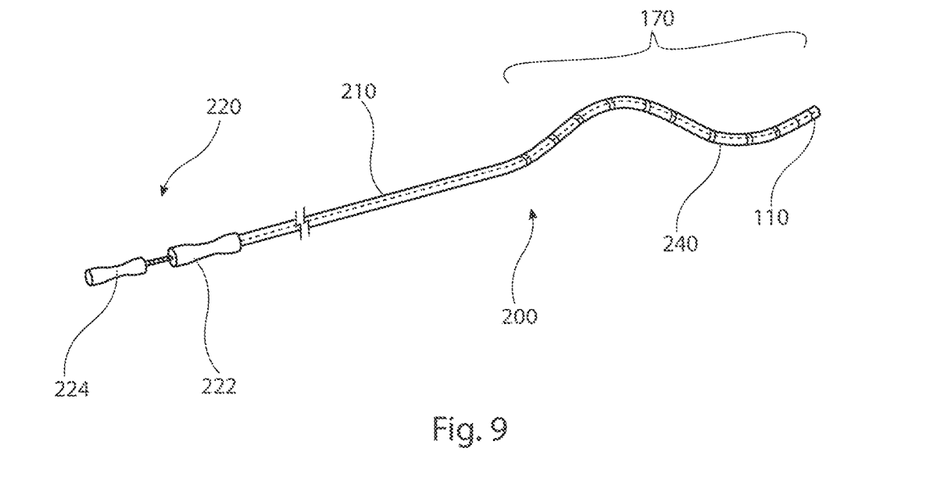
FIG. 9 is a schematic diagram of an example of guide wire assembly as taught herein.

With reference also to FIG. 9, this shows in schematic form the locking arrangement for the guide wire 200 and also the principal elements of an example of control handle 220. Disposed within the lumen 90 of the guide wire 200 is a locking element 240 which may be a wire or cable, fixed at the distal end 202 of the guide wire and passing through to the handle 220. The wire may be made of metal, carbon fibre, plastics material such as silicone or the like and may be single stranded or multi stranded, as preferred.

In the embodiment shown in FIG. 9 the proximal end of the locking element 240 is coupled to a handle element 224 of the handle assembly 220, which in its simplest form can be moved towards and away from a part of the handle 222 fixed relative to the catheter 210. Moving the locking handle portion 224 towards the fixed handle portion 222 loosens the locking element 240 and therefore loosens the connection between the segments or elements of the guide wire, enabling them to rotate relative to one another. On the other hand, moving the locking handle portion 224 away from the fixed handle portion 222 will tense the locking element 240, which in practice will pull the segments of the guide wire assembly towards one another, in the direction of the arrows a in FIGS. 2 and 3. This will cause the facing surfaces of the segments of the guide wire to press against one another and to lock to one another by way of friction or mechanical engagement. Once locked, the segments of the guide wire will not be able to rotate and the guide wire will therefore remain in that configuration. There may be provided a spring or other biasing mechanism between the handle portions 222 and 224 to bias them apart from one another and therefore the assembly into a locked condition. The main portion of the catheter 210 may be of a conventional flexibility, that is able to curve inside a patient's vasculature but being sufficiently strong to provide pushing and torque strength.

It is to be appreciated that FIG. 9 shows a simple example of a locking mechanism and that in place of a spring other mechanisms could be used, such as a motor, a solenoid, a screw fitting, and so on. Any mechanism which is able to pull back the wire so as to tighten the pivoting/rotating elements of the guide wire can be used.

In use, the guide wire can be fed endoluminally through a patient's vasculature, with the locking element in its unlocked condition, that is with the segments able to rotate relative to one another, such that the guide wire is very flexible. In this condition, the guide wire can pass through tortuous vasculature and also through delicate vessels including, for example, the neural vessels.

It will be appreciated that the elements or segments will rotate relative to one another to give the segmented portion of the guide wire a complex curved shape, in dependence upon the direction of curvature and bending of the vessels through which it passes. The guide wire can be locked in the configuration in which it is variably curved, by pulling on the locking mechanism. This fixes the segments relative to one another. Locking can be done for a variety of reasons. For instance, the guide wire elements can be locked relative to one another to assist in feeding the guide wire through a patient's vasculature, for example for directing the distal end of the guide wire through a bifurcation or into a branch vessel. After positioning, the guide wire sections can be unlocked again. The guide wire can also be locked into its configuration once it has been positioned within a patient's vessels up to the site at which treatment is to be carried out, so as to support an introducer assembly passed through the patient's vasculature over the guide wire.

Figure 10:
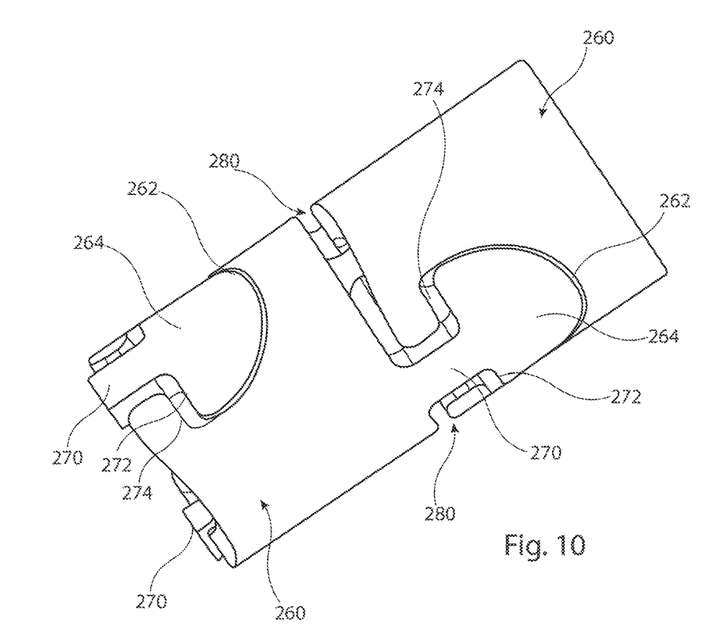
FIGS. 10 and 11 are perspective views of another embodiment of guide wire assembly.
Figure 11:
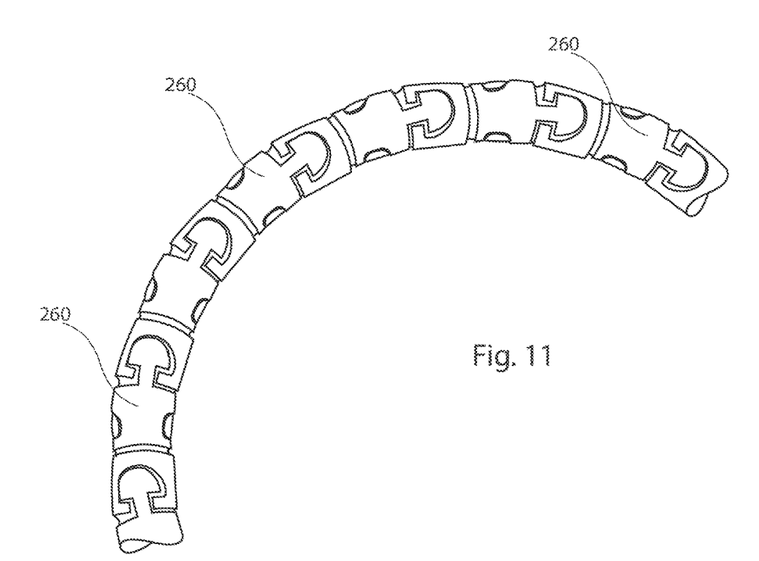

Referring now to FIGS. 10 and 11, these show another embodiment of link mechanism, that is of inter-cooperating elements for a guide wire having the characteristics taught herein. The embodiment of FIGS. 10 and 11 has numerous similarities with the embodiments of FIGS. 2 to 9. The primary difference lies in the shape of the cooperating surfaces, as described below and as shown in the drawings. Referring first to FIG. 10, this shows in part of three interconnected elements 260 forming the distal end of the guide wire. As can be seen from FIG. 10, in this embodiment each inter-cooperating element is of tubular form, similar to the previously described embodiments, and has a male part 264 with a rounded facing surface, as well as a female recess 262 with a cooperating rounded surface. The male elements 264 include a neck 270 of reduced lateral dimension and a generally perpendicular shoulder 272 either side of the neck 270. The female coupling section 262 has similar perpendicular shoulders 274 and in practice the two shoulders 272, 274 face one another, as can be seen in the drawings. The facing shoulders 272, 274, which are preferably perpendicular or substantially perpendicular to the cylindrical (longitudinal) axis of the elements 260 provide secure attachment of the adjacent elements to one another with no risk of the elements coming apart.

Adjacent inter-cooperating elements 260 have a gap 280, which enables the elements 260 to pivot or rotate relative to one another and which also restricts the rotation on one element with respect to its adjacent element(s).

It will be apparent from FIG. 10 that the male and female parts 264, 262 within each element 260 are offset by 90° relative to one another, thereby enabling each element 260 to rotate in two different directions relative to its two adjacent elements 260 (above and below), giving the assembly a greater number of directions of bending. In other embodiments the offset could be different from 90°. Other examples include any offset angle from around 30° to 90°, such as 60° or 75°.

As with the embodiments described above and elsewhere in this application, the elements 260 can be laser cut from a single tube of material, for example stainless steel or Nitinol. Furthermore, it will be apparent that each element 260 will have two sets of male connectors and female connectors, circumferentially opposite one another.

FIG. 11 shows a portion of a guide wire formed by the elements 260 shown in detail in FIG. 10, and which has been curved in a single plane. As with all of the embodiments described herein, the elements 260 can be locked to one another by tightening the internal locking mechanism, that is the wire which extends through the lumen of the guide wire from its distal end to an external manipulation portion for assembly of the guide wire. The facing surfaces 262 and 264 will lock to one another by virtue of the mechanisms described herein in connection with the other described embodiments and which need not be repeated here.

Figure 12:
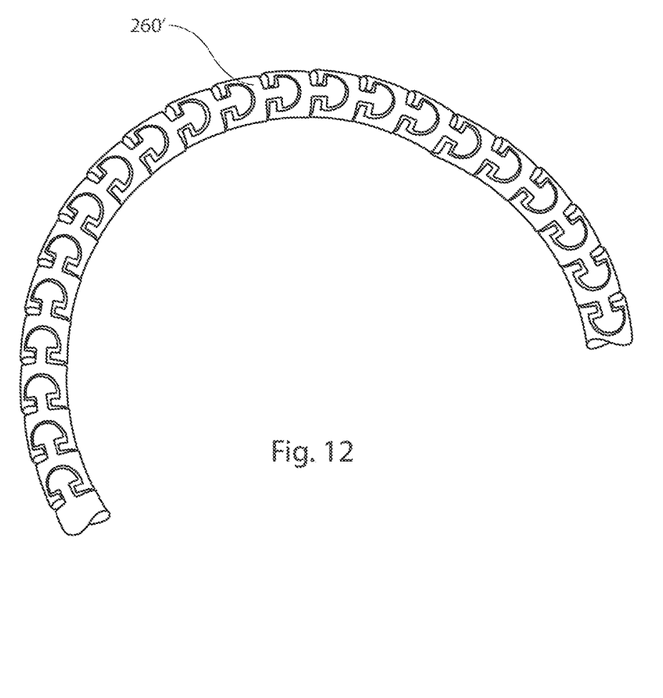
FIGS. 12 and 13 are perspective views of another embodiment of guide wire assembly similar to the embodiment of FIGS. 11 and 12.
Figure 13:
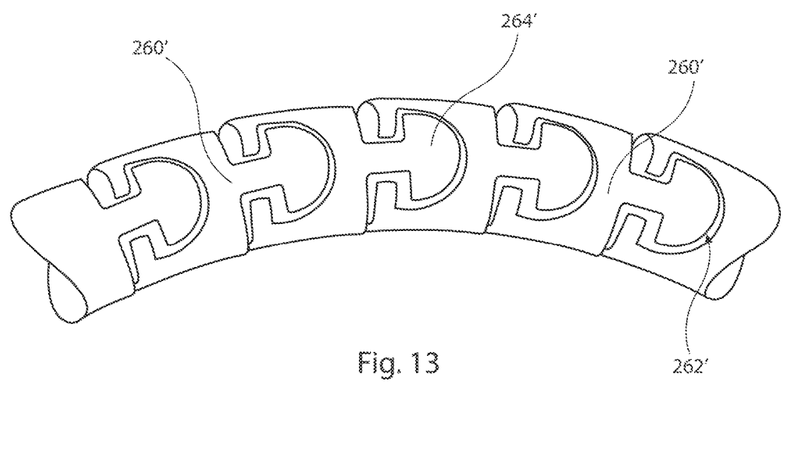

Referring now to FIGS. 12 and 13 these show another embodiment guide wire having inter-cooperating elements 260' that have male and female connecting elements of the same form as those of FIGS. 10 and 11, but in which the male and female connecting elements 262', 264' of each element 260' are circumferentially aligned with one another rather than being 90° offset (or other offset). This gives the guide wire a degree of bending in a single plane.

As the elements 260' of the embodiments of FIGS. 12 and 13 have equivalent characteristics to those of the previously described embodiments, they are not described in any further detail herein.

In practice, therefore, the assemblies taught herein can provide a very soft guide wire which is able to be locked into a shape during the procedure. The guide wire will retain that shape and in effect become stiff when so locked. This can provide more optimal support for a microcatheter introduced over the guide wire. The guide wire can be manipulated, unlocked, to become soft again and this can be controlled entirely by the clinician and repeated over and again during the procedure. In other words, the guide wire can be unlocked and locked repeatedly as required.

The elements or segments of the guide wire of the above described can be made from laser cut tube formed from any suitable material, for example stainless steel, Nitinol and the like.

The segments can have features (enlarged heads and cut-outs) radially offset to one another by up to 90° and in some embodiments offset in a range from 0-90°, as deemed appropriate. Of course, different sets of segments within the same guide wire could have different offsets.

The guide wire may have an outer diameter in the region of 0.35 mm to around 0.9 mm for neurovascular procedures but could equally have greater diameters, for instance of a millimeter or more, for other vessels. The porting of the guide wire formed of inter-cooperating elements may have a length of a few centimeters up to around 5 to 10 centimeters in some instances. The skilled person will appreciate that in many cases it is a design choice how long to make the lockable part of the guide wire.

It is envisaged that in some embodiments the segmented portion of the guide wire at least may be covered with a thin protective sleeve made of a relatively soft material, for example silicone or the like.

It will also be appreciated from the above teachings that the shapes of the recesses and enlarged heads of the segments are such that that segments are not able to separate from one another during use of the guide wire.

All optional and preferred features and modifications of the described embodiments and dependent claims are usable in all aspects taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A medical guide wire of elongate form and having a longitudinal dimension, the medical guide wire comprising:
   a distal end and a proximal end; the distal end of the guide wire being formed of a plurality of inter-cooperating elements disposed longitudinally in series, the inter-cooperating elements having cooperating curved facing surfaces which are able to slide relative to one another such that the distal end of the guide wire is bendable in at least one lateral dimension; wherein the cooperating curved surfaces form a unitary device in which the inter-cooperating elements do not disassemble from one another; wherein the cooperating facing surfaces are lockable in a non-sliding manner to one another, the inter-cooperating elements comprising a male spherical protrusion having a neck of reduced lateral width and a female element defining a spherical concave cavity and having a shoulder extending perpendicularly relative to an axis of the inter-cooperating element, toward the male element and proximate to the neck, wherein the spherical protrusion and the spherical concave cavity are each greater than semi-spherical; and
   a locking element coupled at the distal end of the guide wire and operable to lock the cooperating facing surfaces together such that the distal end of the guide wire is lockable in a straight configuration and a bent configuration.

2. A medical guide wire according to claim 1, including three inter-cooperating elements having a plurality of sets of cooperating surfaces, each set of cooperating surfaces being located at an adjacent one of the three inter-cooperating elements.

3. A medical guide wire according to claim 2, wherein the sets of cooperating surfaces are disposed along a common line parallel to a longitudinal dimension.

4. A medical guide wire according to claim 2, wherein the sets of cooperating surfaces are disposed on an outer surface of the inter-cooperating elements along different lines parallel to a longitudinal dimension.

5. A medical guide wire according to claim 1, wherein the locking element applies a longitudinally extending constraining force on the inter-cooperating elements.

6. A medical guide wire according to claim 1, wherein inter-cooperating elements each have a channel therein, the channels being arranged in series with one another.

7. A medical guide wire according to claim 6, wherein the locking element is disposed in the channels of the inter-cooperating elements.

8. A medical guide wire according to claim 7, wherein the locking element is a wire or cable connected at the distal end of the guide wire.

9. A medical guide wire according to claim 8, wherein the locking element is connected to a driving element at the proximal end of the guide wire.

10. A medical guide wire according to claim 9, wherein the locking element is made of a metal or metal alloy.

11. A medical guide wire according to claim 9, wherein the locking element is made of carbon fiber.

12. A medical guide wire according to claim 6, wherein the locking element is made of a stretchable material.

13. A medical guide wire according to claim 12, wherein the locking element is made of an elastomeric material.

14. A medical guide wire according to claim 1, including a covering or sleeve disposed over the inter-cooperating elements.

15. A medical guide wire of elongate form and having a longitudinal dimension, the medical guide wire comprising:
    a distal end and a proximal end; the distal end of the guide wire being formed of a plurality of inter-cooperating elements disposed longitudinally in series, the inter-cooperating elements having cooperating male elements and female elements which are able to slide relative to one another such that the distal end of the guide wire is bendable in at least one lateral dimension, the male elements comprising a spherical protrusion and the female elements comprising a spherical concave surface, wherein the spherical protrusion and the spherical concave surface are each greater than semi-spherical and are configured to trap the male elements within the female elements and prevent separation between the male elements and the female elements; and the male elements and the female elements are lockable in a non-sliding manner to one another; and
    a locking device coupled at the distal end of the guide wire and operable to lock the male elements and the female elements together such that the distal end of the guide wire is lockable in a straight configuration and a bent configuration.

16. The medical guide wire of claim 15, wherein the spherical concave surface extends beyond a maximum diameter of the spherical protrusion.

17. The medical guide wire of claim 15, wherein the spherical protrusion and the spherical concave surface each comprise an arrangement of interlocking teeth.

* * * * *